United States Patent
Ramaut

[19]

[11] Patent Number: 6,100,684
[45] Date of Patent: Aug. 8, 2000

[54] HELICALLY TRAVELING NON-DESTRUCTIVE SYSTEM FOR THE DETECTION OF CRACKS IN PIPELINES

[75] Inventor: Edouard Ramaut, Villepreux, France

[73] Assignee: Societe des Transports Petroliers par Pipeline Trapil, Paris, France

[21] Appl. No.: 09/063,400

[22] Filed: Apr. 21, 1998

[30] Foreign Application Priority Data

Apr. 21, 1997 [FR] France ................................... 97 04902

[51] Int. Cl.$^7$ ................................................. G01N 27/82
[52] U.S. Cl. ........................... 324/220; 324/228; 324/235
[58] Field of Search .................................. 324/220, 221, 324/228, 235; 73/592, 623

[56] References Cited

U.S. PATENT DOCUMENTS

| | | |
|---|---|---|
| 4,072,894 | 2/1978 | Barton . |
| 4,468,619 | 8/1984 | Reeves ..................................... 324/220 |
| 4,675,604 | 6/1987 | Moyer et al. . |
| 5,293,117 | 3/1994 | Hwang ...................................... 324/220 |
| 5,532,587 | 7/1996 | Downs et al. ............................ 324/220 |
| 5,565,633 | 10/1996 | Wernicke ............................. 324/220 X |
| 5,751,144 | 5/1998 | Weischedel ........................... 324/220 X |
| 5,864,232 | 1/1999 | Laursen .................................... 324/220 |

FOREIGN PATENT DOCUMENTS

WO 97/12237  4/1997  WIPO .

*Primary Examiner*—Gerard Strecker
*Attorney, Agent, or Firm*—Pollock, Vande Sande & Amernick

[57] ABSTRACT

A helically movable system for the detection of cracks in a pipeline, capable of moving inside this pipeline, produces a magnetic flux that passes into a portion of the pipeline. Detectors measure local magnetic fields on the inner surface of the pipeline. These measurements are provided for processing and storage. The system is driven by the fluid flowing in this pipeline. Devices for the generation of flux and the measuring are arranged within at least one cylindrical housing having wheels to make this housing follow a substantially helical path inside the pipeline.

12 Claims, 5 Drawing Sheets

HELICALLY TRAVELING NON-DESTRUCTIVE SYSTEM FOR THE DETECTION OF CRACKS IN PIPELINES

BACKGROUND OF THE INVENTION

1. Field of the Invention

The present invention relates to a system to detect cracks and variations of thickness in pipelines. It relates especially to a method of detection implemented in this system. The pipelines considered herein are cylindrical and are made of an alloy or material that contains a significant proportion of ferromagnetic elements. They are mainly pipelines made of steel or iron.

Oil pipelines have to be regularly inspected for the appearance of cracks, arising partly out of corrosion or fatigue, in order to avert the possible risk of their breaking. The incipient cracks may be very small, have all sorts of shapes and be oriented in different directions. The main problem with this kind of inspection is that it is necessarily performed on site and from inside the pipelines, in portions where these pipelines are buried.

2. Description of the Related Art

Apart from ultrasonic and X-ray detection systems, there presently exists a system for the magnetic detection of cracks in a pipeline comprising a traction module and a magnetic detection module. The traction module is provided with peripheral joints and is driven by the flow of liquid flowing in the pipeline. The module may contain electronic processing circuitry, electrical power storage means and recording equipment. The magnetic detection module comprises an axial permanent magnet or magnets and, at each of its ends, brushes made of a ferromagnetic material that set up a magnetic path for the magnetic flux generated by the permanent magnets which thus gets closed in through a portion of the pipeline. The magnetic detection module is provided on its periphery with a set of Hall detectors or other detectors providing measurement signals that represent the magnetic induction on the inner surface of the pipeline. These measurement signals, which are acquired permanently during the movement of the detection system inside the pipeline, are used to obtain a magnetic signature of this pipeline.

This detection system, provided with a sequence of articulated modules and an odometer device, is inserted into a pipeline from an entry point called a siding. The pipeline which has been drained beforehand to enable the opening of the circuit and the introduction of the system is then put back into operation with a circulation of fluid. The detection of the weld joints located at predetermined distances associated with the odometry measurement enables the detected variations of thickness and cracks to be localized.

This system is used to detect cracks whose main orientation is substantially perpendicular to the axis of the pipeline. However, this system cannot be used to detect cracks that are oriented in a direction almost parallel to the axis of the pipeline and are shallow. For, the variation in the swept flux caused by this type of crack is generally far too small to be detected.

SUMMARY OF THE INVENTION

The present invention is aimed at overcoming this drawback by proposing a system of detection that is capable of detecting cracks oriented substantially along the axis of a pipeline while at the same time having the characteristics of autonomy of prior art systems.

This goal is achieved with a pipeline crack detection system that is capable of moving within this pipeline, said system comprising:

means to generate and inject a magnetic flux into a portion of the pipeline, means to measure local magnetic fields on the inner surface of the pipeline, means to process these measurements, store them and localize them, and means to drive this system by the flux of fluid flowing in this pipeline.

According to the invention, the means for the generation and injection of magnetic flux and the measuring means are arranged within at least one substantially cylindrical measurement set comprising guidance means to make this measurement set follow a substantially helical path inside the pipeline.

With the crack detection system of the invention, it becomes possible to detect anomalies of thickness, cracks and longitudinal crevices. The magnetic field generated by the magnets and injected into the pipeline is henceforth oriented transversally and its movement is helical. Furthermore, the flows of flux are henceforth localized on sliding angular sectors.

In a preferred embodiment of a system according to the invention, the measurement set comprises a plurality of magnetic circuits positioned evenly on the periphery of said measurement set, each magnetic circuit comprising a yoke made of ferromagnetic material, the yoke comprising two poles directed towards the inner surface of the pipeline, each pole being provided with permanent magnets, these permanent magnets being arranged so that two adjacent poles belonging to two distinct magnetic circuits have one and the same polarity.

The measurement set furthermore comprises, by way of magnetic field measurement means, Hall detector sets or the like positioned between the poles of each yoke.

Each set of detectors is preferably integrated into a part made of insulating material positioned on the periphery of the measurement set.

In a preferred version of the invention, the guidance means comprise free wheels located on the periphery of the measurement set and having a predetermined orientation to provide for a helical path.

The free wheels may be arranged for example in several longitudinal rows positioned in housings made on the periphery of the measurement set. In particular, rows of wheels may be located between the respective poles of each magnetic circuit. Thus, in a practical embodiment, each row of wheels is positioned between a pole of the magnetic circuit and a set of detectors. At each of its ends, the measurement set furthermore comprises a set of end guidance wheels arranged so as to contribute to the helical path of the measurement set in substantially rectilinear portions or with a very wide radius of curvature of the pipelines.

A detection system according to the invention is formed in practice by a sequence of several sets connected to one another by linking means, in particular at least one drive unit containing the processing and recording means and at least one measurement set. It furthermore comprises at least one rotating contact set positioned between the measurement set or sets and the drive unit or units.

This system comprises at least two successive measurement sets so that, in overlapping, they scan the entire inner surface of the pipeline.

According to another aspect of the invention, there is proposed a method to detect cracks in a pipeline, implemented in a system according to the invention, comprising:

a local generation of magnetic flux along the pipeline, measurements of local magnetic fields on the inner surface of the pipeline, a processing of these measurements in order to store them and localize them, a driving of this system by the flux of fluid flowing in this pipeline, wherein the local generation of magnetic flux and the measurements of magnetic fields are performed on helical paths on the inner surface of the pipeline.

It is of course possible to provide for combining a prior art system for the detection of transversal cracks with a detection system according to the invention.

BRIEF DESCRIPTION OF THE DRAWINGS

Other special features and advantages of the invention shall appear from the following description and from the appended drawings, given by way of nonrestrictive examples. Of these drawings.

MORE DETAILED DESCRIPTION

An exemplary embodiment of a measurement set unit and a detection system including this measurement set, along with the crack detection method implemented in this system, shall now be described with reference to the above-mentioned figures.

Figure 1:
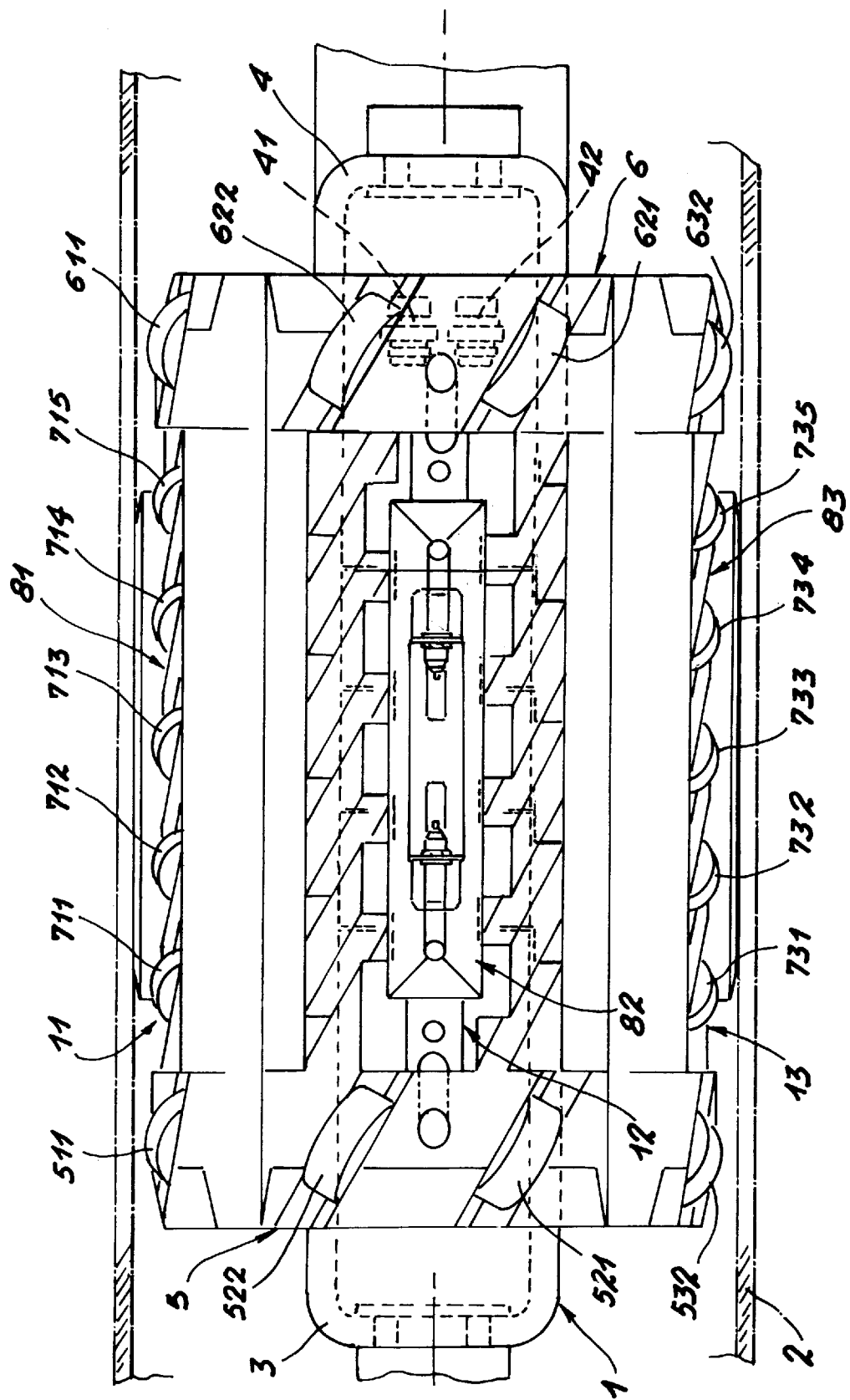
FIG. 1 is a top view of a measurement set implemented in the invention.
Figure 3:
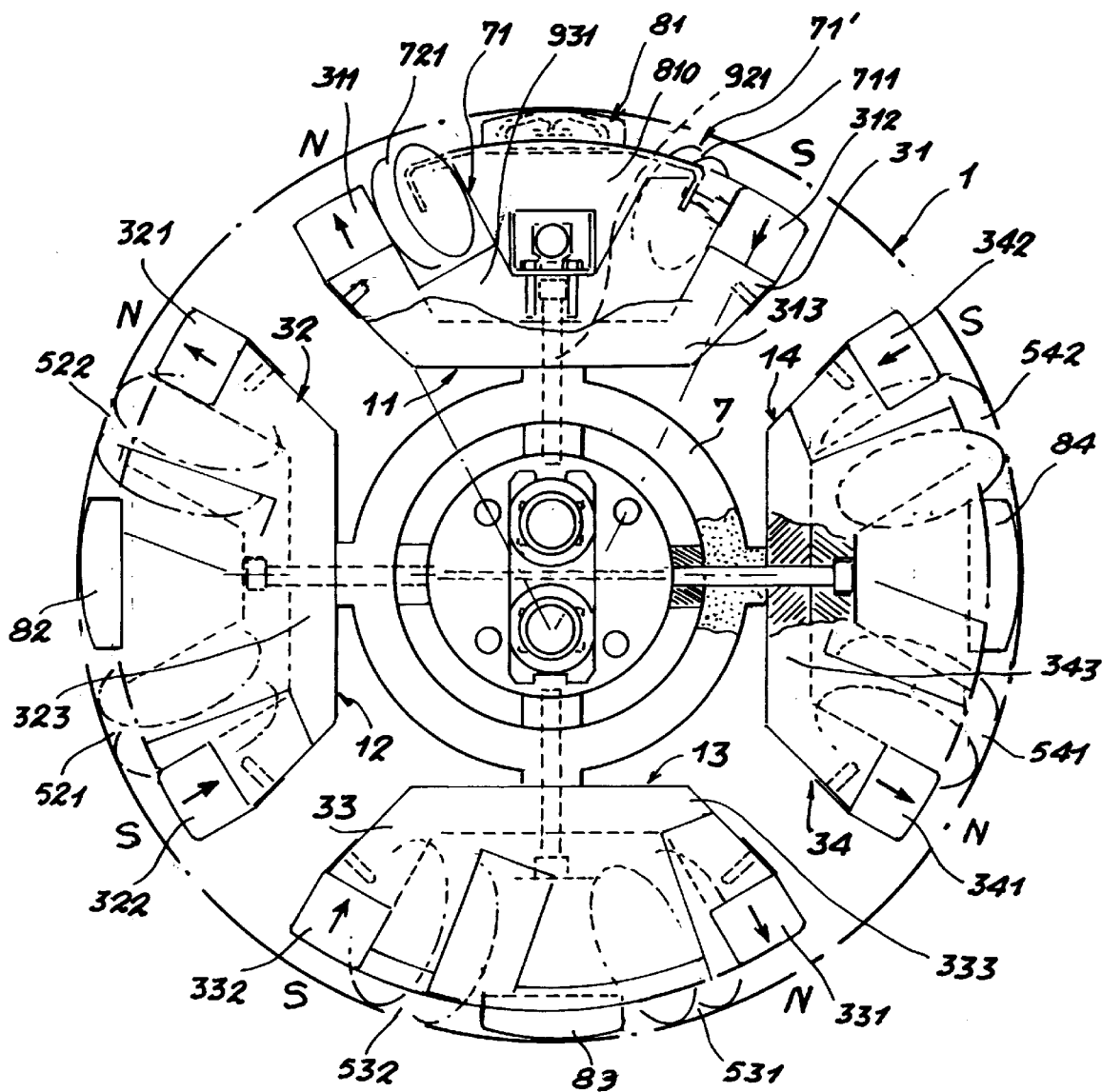
FIG. 3 illustrates the internal structure of this measurement set.

The measurement set (unit) 1 shown in FIG. 3 comprises a central structure 7 to which four measurement modules 11, 12, 13 and 14 are fixed and spaced out angularly by 90°. It also comprises two end modules 5, 6 (FIG. 1). Each measurement module 11–14 comprises a C-shaped or U-shaped yoke 31, 32, 33, 34 made of ferromagnetic material, comprising two poles directed towards the exterior of the measurement set and therefore towards the interior of the pipeline 2 in which the detection system according to the invention operates. The two poles of each yoke 31–34 are provided, in one case, with a permanent magnet producing a magnetic flux directed outwards (North Pole) 311, 321, 331, 341, and, in the other case, with a permanent magnet producing a magnetic flux pointed inwards (South Pole) 312, 322, 332, 342. The permanent magnets are positioned on the outer surface of the measurement set so that two adjacent permanent magnets belonging to two distinct adjacent yokes have one and the same polarity in order to prevent any effect of leakage and coupling between neighboring yokes.

Each measurement module 11–14 furthermore comprises a guidance piece 931 made of non-magnetic material arranged so as to receive two rows 71, 71' of guidance wheels 711–715, 731–735, oriented so that their rotation along the inner wall of the pipeline leads to a helical path of the measurement set 1. Each measurement module 11–14 is fixed to the central structure 7 by a set of screws 921.

Figure 2:
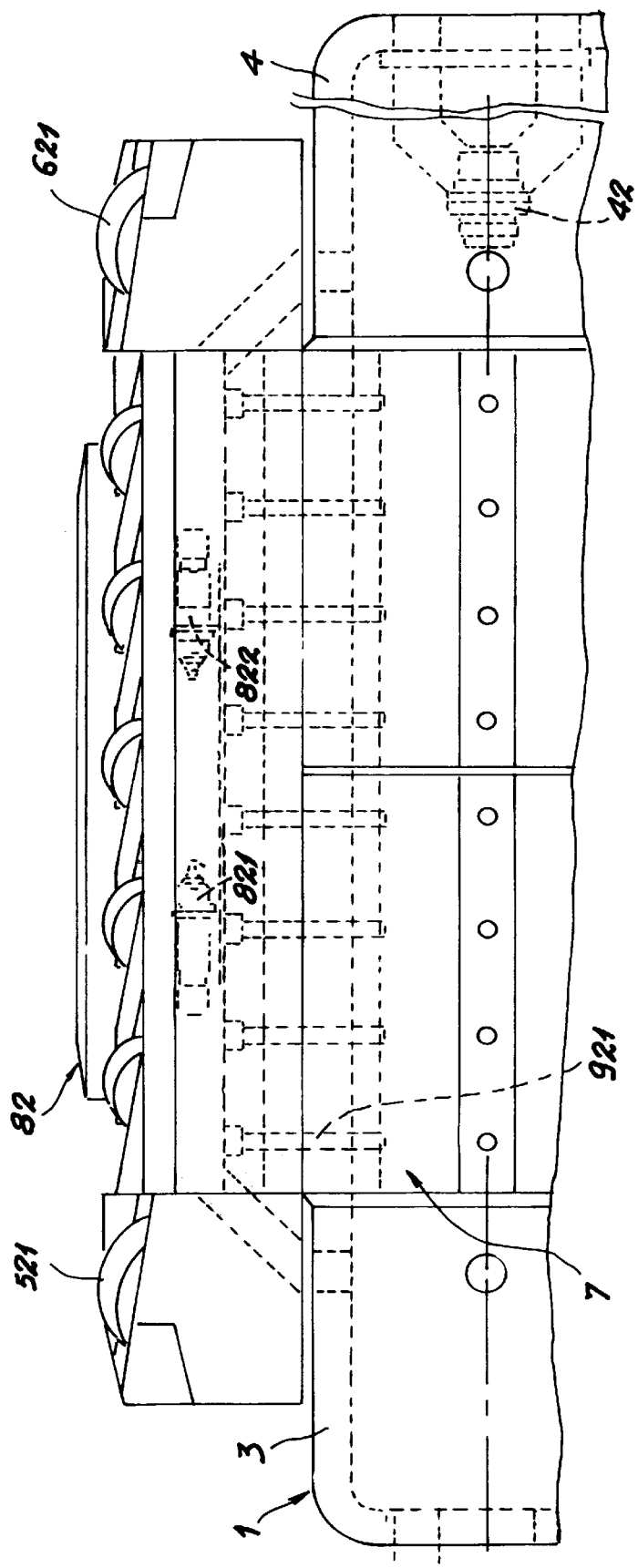
FIG. 2 is a partial sectional view of the measurement set of FIG. 1.

Each end module 5, 6 has four groups of guidance wheels 511, 521, 522; 531, 532; 541, 542; 611, 621, 622, 632. These wheels have a diameter substantially greater than that of the guidance wheels positioned in the rows of wheels that are positioned in the measurement modules. Each measurement module 11–14 is furthermore provided with a set of Hall detectors or other types of detectors contained in a detection rod 81–84, positioned longitudinally to the periphery of the measurement set 1 so as to be in the immediate vicinity or even in contact with the inner surface of the pipeline 2. Each detection rod 81–84 is fixed to a supporting part 810 made of non-magnetic material itself fixed to the guidance part 931. The Hall detectors are connected to the electronic measurement circuitry and to the storage equipment located in a drive unit through connecters 821, 822 (FIG. 2) designed to be the measurement set 1 and linking cables and connectors (not shown).

Figure 4:
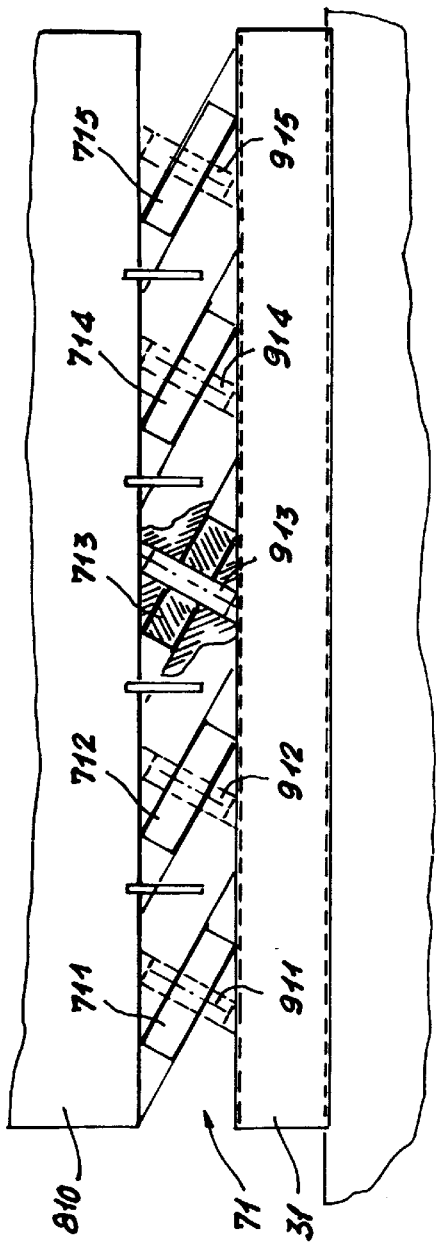
FIG. 4 illustrates a detail of an embodiment of a row of wheels in a measurement set.

Each row of wheels 71 is placed between a supporting part 810 and an arm of a yoke 31, as shown in FIG. 4. A row 71 has for example five wheels 711–715 positioned longitudinally and having parallel axes of rotation 911–915 inclined for example by an angle of 30° with respect to a diametrical axis. The choice of this angle of orientation directly conditions the pitch of the helix described by the measurement set and the length of the detection rods.

Furthermore, at each of its ends, the measurement set 1 comprises mechanical linking equipment 3, 4 and electrical linking equipment 41, 42 for linkage with the other neighboring units within the detection system according to the invention.

It must be noted that, with the exception of the yokes, all the components of the measurement set must be made out of non-magnetic materials. Furthermore, the parts located in the immediate vicinity of the flows of magnetic flux must be preferably made of an electrically non-conductive material, for example a synthetic material, in order to prevent any appearance of eddy currents during variations in leakage flux in these parts, which could possibly induce disturbances in the measurements.

In a practical embodiment, a detection rod may have 18 Hall-effect detectors. As a non-restrictive example, the pitch of the helical movement may be about 2 m, with an angle of 30°. The Hall detector bars may have a length of 20 cm.

Figure 5:
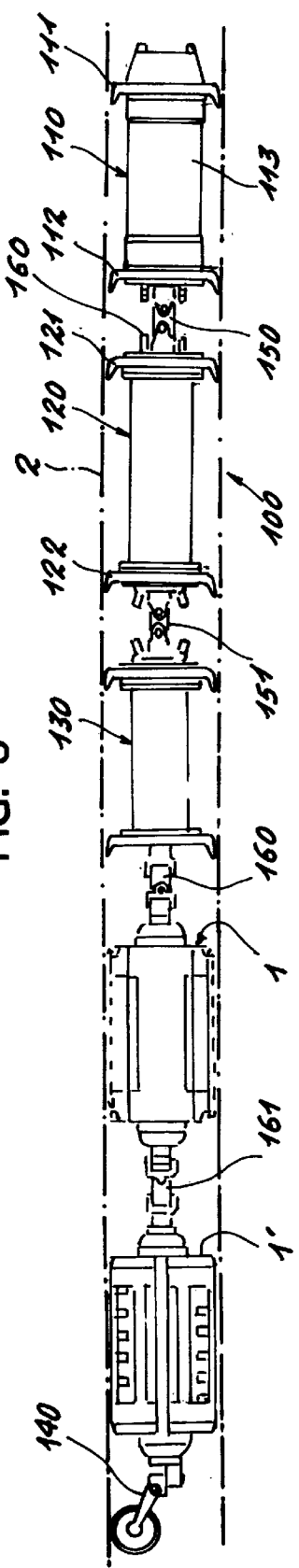
FIG. 5 shows an exemplary implementation of a detection system according to the invention, in a straight portion of a pipeline.
Figure 6:
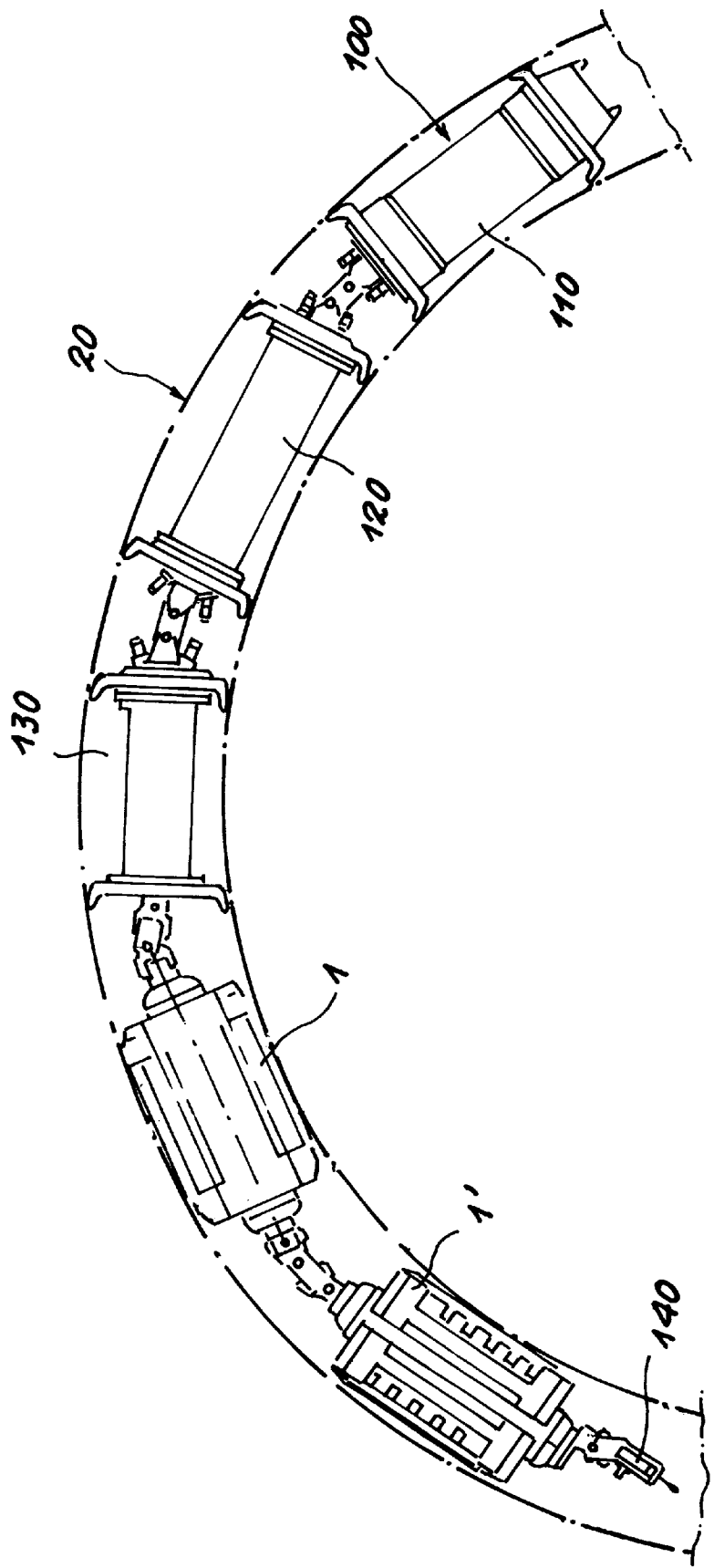
FIG. 6 shows a characteristic situation of a detection system in a curved portion of a pipeline.

A description shall now be given of an exemplary embodiment of a detection system according to the invention, with reference to FIGS. 5 and 6. A crack detection system 100 according to the invention may include, with reference to FIG. 5, a first drive unit 110 includes a cylindrical housing 113 containing electrical power cells, a second drive unit 120 containing the electronic measurement circuitry, a set of rotating contacts 130, a first measurement set 1 and a second measurement set 1' and a counting and odometer set 140.

The drive units 110, 120 connected to each other by a mechanical linking device 150 and an electrical linking device 160 (partially shown) are provided with joints 111, 112; 121, 122. These joints contribute to the onward movement of the system through the pressure on them by the fluid flowing in the pipeline 2. The set of rotating contacts, connected to the second drive unit 120 by mechanical linking devices 151 and electrical linking devices, provides for electrical power connections and the transmission of signals between the drive units which do not rotate and the two measurement sets which, for their part, follow a helical path within the pipeline and therefore rotate on themselves. The set of rotating contacts 130 may be made by standard techniques using, for example, conductive tracks and slipring brushes on these tracks. The two measurement sets 1, 1' are connected to each other and to the set of rotating contacts 130 by cardan type linking devices 160, 161. The counting unit 140 may be made in the form of a disk kept in a rolling motion on the inner surface of the pipeline. This disk is pierced for example with holes and is associated with a pulse counter cell. It must be noted that it is advantageously possible to make use of the detection of the weld joints at the junction between two pipeline portions to obtain positional references for the system within the pipeline and to localize any thickness anomalies that might be detected.

The use of two adjacent measurement sets enables them to overlap each other and thus scan the totality of the pipeline being inspected. It is advantageously possible to provide for a spatial phase shift between the two measurement sets with respect to each other in order to obtain this overlapping.

A description shall now be given of the essential characteristics of the operation of the detection system according to the invention and of the method implemented in this system, especially with reference to FIGS. 5 and 6.

First of all, the detection system according to the invention is introduced, at a siding or branch node, into a pipeline to be inspected. The system is introduced with the pressure turned off. It must be noted that the detection system according to the invention is entirely autonomous. Its cells contained in the first drive unit supply electrical power to all the electrical and electronic equipment. Furthermore, the electronic circuitry installed in the second drive unit comprises a recording unit capable of storing all the measurements made during an inspection and the information on localization in a pipeline.

As soon as the pressure is turned on in the pipeline, the detection system according to the invention is carried along by the fluid. It must be noted that, in substantially rectilinear portions of the path (FIG. 5) or in portions with a great radius of curvature, it is essentially the guidance wheels of the end guidance modules that are in rolling contact on the inner surface of the pipeline. On the contrary, for very small radii of curvature (FIG. 6), it is essentially the rows of central wheels that are active in the inner part of the curvature, and the end wheels are then no longer in contact with the inner surface of the pipeline.

The measurement sets follow a helical path enabling the Hall detection rods to carry out a 360° scan of the inner surface of the pipeline while at the same time having an axial component in their movement. Through a localized magnetic structure obtained by the implementation of four independent yokes, the magnetic fluxes injected into the mass of the pipeline are local and transversal.

The Hall detection rods can thus detect longitudinally oriented anomalies of thickness. This could not be done by the prior art detection system using a longitudinal magnet. It must be noted that it is quite possible to set up a detection system which, in addition to the rotating measurement sets such as those just described for the detection of longitudinal cracks and anomalies of thickness, comprises a measurement set with longitudinal magnets for the detection of transversal cracks. This would make it possible to obtain a full mapping of the magnetic signatures of a steel or iron pipeline. The detection system according to the invention is normally retrieved at another siding or branch node after it has travelled through a specified route within the pipeline to be inspected. The data elements recorded are then processed to provide characteristic signatures of the condition of the pipeline.

Naturally, the invention is not limited to the examples that have just been described and many improvements can be made to these examples without departing from the context of the invention. Thus, it is possible to design other arrangements of measurement sets, especially with a different number of measurement modules and another angle of tilt of the guidance wheel. Furthermore, the number of drive units is not limited to that of the system just described. Thus, it is possible to provide for one drive unit that includes for example both the electronic measurement circuitry and the power cells. Moreover, it is possible to envisage other techniques of odometry than those just described.

It is possible especially to place the power cells and measurement electronic circuit within the rotating measurement set, thus preventing the use of rotating contacts.

The particular exemplary embodiment has been described with hall-effect type detectors, but it is clear that detectors of different types may also be implemented.

What is claimed is:

1. A system for the detection of cracks and anomalies of thickness in a cylindrical pipeline that can be inserted into and moved within this pipeline, said system having at least one cylindrical measurement unit comprising:

a plurality of magnetic means for producing and injecting a transversal magnetic flux into a portion of the pipeline, means to measure local magnetic fields, produced by the magnetic means, on the inner surface of the pipeline, means to drive this system by the movement of fluid flowing in this pipeline, the means for production and injection of flux and the measuring means being arranged within the substantially cylindrical measurement unit that further includes guidance means to make the measurement unit follow a substantially helical path inside the pipeline, wherein the magnetic means are circumferentially spaced evenly around the periphery of said measurement unit, each magnetic means comprising a yoke made of ferromagnetic material, the yoke comprising two poles directed towards the inner surface of the pipeline and each being provided with permanent magnets, these permanent magnets being arranged so that two adjacent poles belonging to two distinct magnetic means have one and the same polarity.

2. A system according to claim 1, wherein the measurement unit further includes at least one detector for the detection of pipeline cracks and thickness anomalies by variations from the measurement means positioned between the poles of each yoke.

3. A system according to claim 2, wherein detector is integrated into a part made of insulating material positioned on the internal periphery of the measurement unit so as to be in contact with or in the immediate vicinity of the inner surface of the pipeline.

4. A system according to claim 2 wherein the detectors are Hall-effect type devices.

5. A system according to claim 1, wherein the guidance means comprise free wheels located on the periphery of the measurement unit, each having a predetermined running direction to give the measurement unit a helical path in the pipeline.

6. A system according to claim 5, wherein the free wheels are arranged in several longitudinal rows positioned on the periphery of the measurement unit.

7. A system according to claim 6, wherein the rows of wheels are located between the respective poles of each magnetic circuit.

8. A system according to claim 7, wherein the guidance means furthermore comprise, for each yoke, a part to support two rows of wheels positioned respectively between a pole of the magnetic means and a detector device.

9. A system according to claim 5, wherein the housing furthermore comprises, at each of its ends, a set of end guidance wheels arranged so as to contribute to the helical path of the housing in a pipeline.

10. A system according to claim 1 further including at least one additional unit linked to the first unit, the additional unit being a drive unit containing processing and recording means, said system further comprises at least one rotating contact set positioned between the first and additional units.

11. A system according to claim 10, comprising at least two first housings so that, in overlapping, they scan the entire inner surface of the pipeline.

12. A system according to claim 10 further comprising a measurement unit enclosing longitudinally spaced magnet means and corresponding longitudinally spaced detectors positioned on the periphery of the unit, the longitudinally spaced magnets and detectors achieving detection of transversally oriented pipeline cracks.

* * * * *